United States Patent
Konoske et al.

(10) Patent No.: US 12,074,923 B2
(45) Date of Patent: Aug. 27, 2024

(54) SYSTEM AND METHOD OF ENABLING AUDIO CONFERENCING IN LIEU OF VIDEOCONFERENCING

(71) Applicant: Doximity, Inc., San Francisco, CA (US)

(72) Inventors: Jeremiah Konoske, Davis, CA (US); Emiliano Zilocchi, Cordoba (AR); Robert Malko, Atlanta, GA (US)

(73) Assignee: Doximity, Inc., San Francisco, CA (US)

( * ) Notice: Subject to any disclaimer, the term of this patent is extended or adjusted under 35 U.S.C. 154(b) by 19 days.

(21) Appl. No.: 17/831,770

(22) Filed: Jun. 3, 2022

(65) Prior Publication Data

US 2023/0396657 A1 Dec. 7, 2023

(51) Int. Cl.
| | |
|---|---|
| *H04L 12/66* | (2006.01) |
| *G16H 80/00* | (2018.01) |
| *H04L 43/0864* | (2022.01) |
| *H04L 65/1089* | (2022.01) |
| *H04L 65/1093* | (2022.01) |
| *H04L 65/403* | (2022.01) |
| *H04M 3/00* | (2024.01) |
| *H04M 3/56* | (2006.01) |

(Continued)

(52) U.S. Cl.
CPC ......... *H04L 65/1089* (2013.01); *G16H 80/00* (2018.01); *H04L 43/0864* (2013.01); *H04L 65/1093* (2013.01); *H04L 65/403* (2013.01); *H04M 3/563* (2013.01); *H04M 3/567* (2013.01); *H04W 4/14* (2013.01)

(58) Field of Classification Search
CPC ............. H04L 65/1069; H04L 65/403; H04L 12/1822; H04L 12/1818; H04L 12/1827; H04L 65/80; H04L 65/1093; H04L 67/306; H04L 67/14; H04L 12/1813; H04N 7/15; H04N 7/147; H04M 3/567; H04M 3/56; H04M 2203/5063; H04M 2201/50
USPC ..... 348/14.08, 14.09, E7.083; 370/352, 260, 370/261; 379/202.01, 158, 93.21, 204.01, 379/88.13; 455/416
See application file for complete search history.

(56) References Cited

U.S. PATENT DOCUMENTS 5,884,039 A * 3/1999 Ludwig ............... H04L 12/1831
348/E7.083
8,059,675 B1 * 11/2011 Cook .................... H04L 67/125
370/464

(Continued)

OTHER PUBLICATIONS

PCT Search Report and Written Opinion from related PCT Application No. PCT/US2023/021724, mailed on Sep. 12, 2023 (12 pages).

*Primary Examiner* — Kharye Pope
(74) *Attorney, Agent, or Firm* — Womble Bond Dickinson (US) LLP (57) ABSTRACT

An apparatus or method implemented in a computer system. In one embodiment the method includes receiving, from a device, a request to join a video call, and determining, in response to receiving the request, whether the device meets predetermined requirements to join the video call via videoconferencing. The method further includes sending, in response to determining the device does not meet the predetermined requirements to join the video call via videoconferencing, a message to the device, wherein the message comprises a link to join the call via audio conferencing.

20 Claims, 7 Drawing Sheets

(51) Int. Cl.
*H04M 5/00* (2006.01)
*H04W 4/14* (2009.01)

(56) References Cited

U.S. PATENT DOCUMENTS

| | | | | |
|---|---|---|---|---|
| 2007/0126861 | A1* | 6/2007 | Kim | H04M 7/0072 348/14.02 |
| 2008/0219223 | A1* | 9/2008 | Bienas | H04L 65/4053 370/338 |
| 2009/0097418 | A1* | 4/2009 | Castillo | H04L 41/12 370/255 |
| 2011/0222466 | A1* | 9/2011 | Pance | H04Q 3/0029 370/316 |
| 2011/0270936 | A1* | 11/2011 | Guthrie | H04L 51/224 379/202.01 |
| 2012/0117250 | A1 | 5/2012 | Santamaria et al. | |
| 2013/0081010 | A1* | 3/2013 | Howell | H04L 67/02 717/173 |
| 2015/0049164 | A1 | 2/2015 | Krishnamoorthy et al. | |
| 2015/0097922 | A1* | 4/2015 | Le Devehat | H04M 3/567 348/14.08 |
| 2015/0116450 | A1* | 4/2015 | Li | H04N 7/147 348/14.12 |
| 2015/0358809 | A1* | 12/2015 | Lau | H04M 7/0072 455/414.1 |
| 2016/0021336 | A1* | 1/2016 | Abbott | H04L 65/1016 348/14.02 |
| 2019/0044984 | A1* | 2/2019 | Chiang | H04L 65/403 |
| 2019/0289042 | A1* | 9/2019 | Perreault | H04L 67/148 |
| 2020/0304547 | A1* | 9/2020 | Lu | H04L 65/1089 |
| 2021/0044635 | A1* | 2/2021 | Archer | H04L 65/403 |
| 2023/0362743 | A1* | 11/2023 | Hwang | H04W 36/00837 |

* cited by examiner

SYSTEM AND METHOD OF ENABLING AUDIO CONFERENCING IN LIEU OF VIDEOCONFERENCING

TECHNICAL FIELD

This disclosure generally relates to video calls. In particular, this disclosure relates to an apparatus and method for joining a video call through audio conferencing when data connectivity problems may prevent joining the video call through video conferencing.

BACKGROUND

Video calls are a common way for people to meet as a group, but without being at the same physical location. Participants can be invited to a video call, and join from their computers or smartphones. Video calls enable participants to see and hear each other, and largely converse as they would during an in-person group meeting.

Video calls are particularly useful for healthcare providers (e.g., doctors, nurses, etc.) and patients. Prior to video calls patients visited health care facilities (e.g., hospitals, clinics, etc.) to receive health related services. With video calls, patients can consult with healthcare providers in the comfort of their own homes.

BRIEF DESCRIPTION OF THE DRAWINGS

Embodiments and implementations of the present disclosure will be understood more fully from the detailed description given below and from the accompanying drawings of various aspects and implementations of the disclosure, which, however, should not be taken to limit the disclosure to the specific embodiments or implementations, but are for explanation and understanding only.

DETAILED DESCRIPTION

Patients can visit with health care providers through video calls if sufficient data connectivity exits between their computing devices and servers that host video calls. If data connectivity is not sufficient, a patient can still join the video call through audio conferencing, which enables audio communication between the health care provider and the patient through, for example, mobile phones or voice over internet protocol (VOIP).

Sufficient data connectivity between patient computing devices and video call servers depends on several variables. For example, the settings of the software (e.g., browser and/or mobile video call application) executing on a patient's computing device (e.g., smartphone or computer) should be compatible with the requirements of the video server that is hosting the video call. The patient's computing device may lack the processing bandwidth to support a video call, or the network connection to the patient's smartphone or computer may not be strong enough to support the video call. Any one of these factors can lead to insufficient data connectivity between the video call server and the patient's computing device. Some patients may not be proficient in the use of computing devices to correct problems that inhibit video calls while they are communicating with their provider.

The present disclosure presents a method and apparatus for detecting data connectivity problems with a patient's computing device. The present disclosure also presents a method and apparatus for placing an audio-only telephone call to the patient when data connectivity problems are detected. While the telephone call does not provide video communication, the telephone call enables audio communication between the patient and the healthcare provider.

Figure 1:
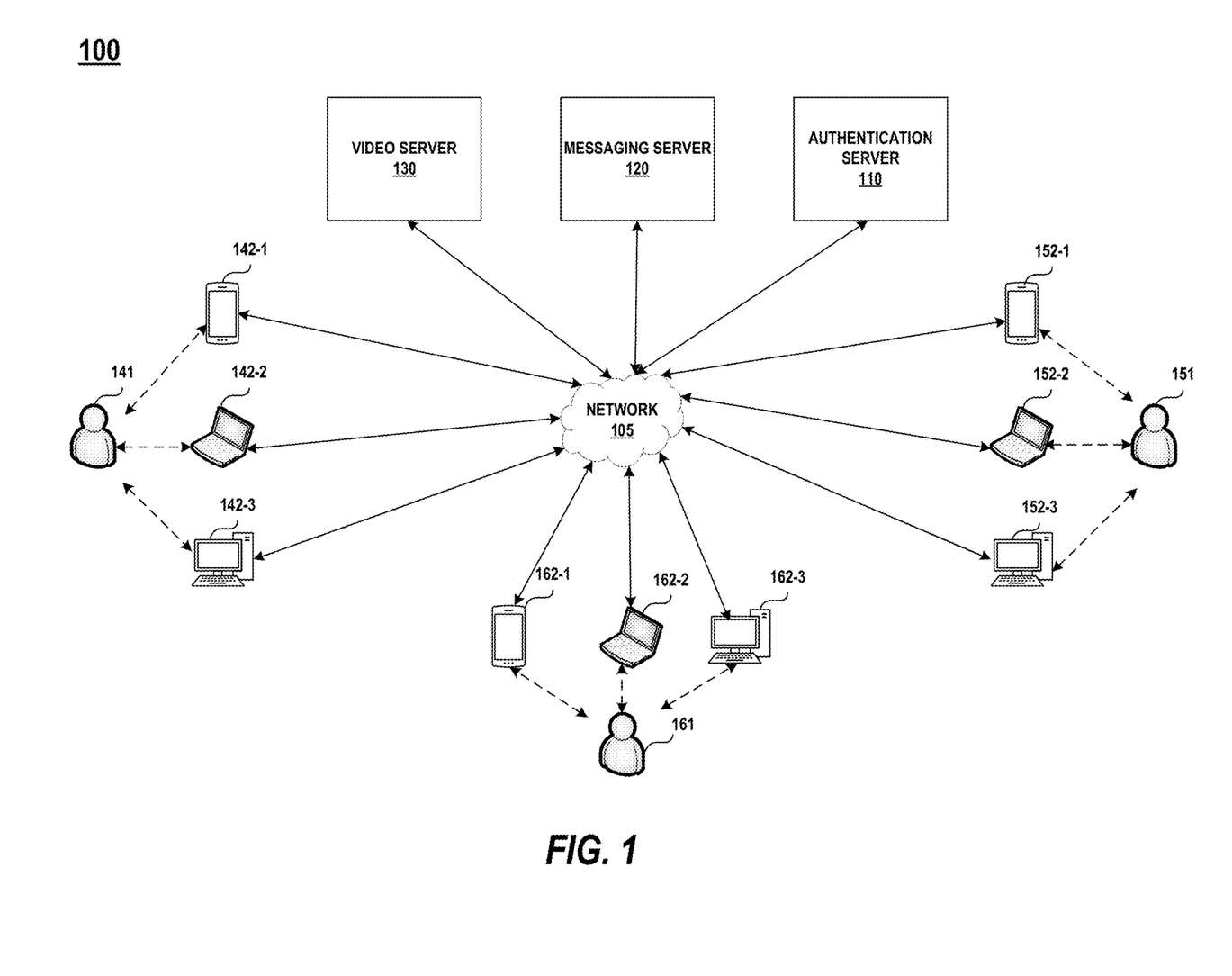
FIG. 1 is a diagram illustrating an example network architecture in accordance with one or more embodiments of the disclosure.

FIG. 1 is a diagram illustrating an example network architecture 100, in accordance with one or more embodiments of the disclosure. The network architecture 100 has a network 105 that includes the Internet, an authentication server 110, a messaging server 120, a video server 130, a patient 141, patient computing devices 142, a healthcare provider 151, healthcare computing devices 152, a service provider 161, and service provider computing devices 162. Examples of computing devices may include, but are not limited to, smartphones, tablet computers, laptop computers, desktop computers, etc. In the illustrated example, patient computing devices 142 include smart phone 142-1, laptop computer 142-2, and desktop computer 142-3. Healthcare provider computing devices 152 include smart phone 152-1, laptop computer 152-2, and desktop computer 152-3. Service provider computing devices include smart phone 162-1, laptop computer 162-2, and desktop computer 162-3.

Healthcare provider 151 may be a person who provides health related services to patient 141. Examples of healthcare providers may include, but are not limited to, doctors, pharmacists, dentists, nurses, therapists, psychologists, technicians, surgeons, etc. Healthcare provider 151 may use any of computing devices 152 to communicate with patient 141 and service provider 161 through a video call hosted on video server 130.

Service provider 161 may provide additional or ancillary services to patient 141. Examples of service providers may include, but are not limited to, insurance providers, translators (e.g., language translators), billing specialists, etc. Service provider 161 may use any of the computing devices 162 to communicate with patient 141 and healthcare provider 151 via the video call.

Patient 141 may use smart phone 142-1, computer 142-2 or computer 142-3 to communicate with healthcare provider 151 and service provider 161 via a video call hosted on the video call server 130, but only if sufficient data connectivity can be established between the computing device 142 and video server 130. Insufficient data connectivity may prevent the video call. Insufficient data connectivity may stem from, for example, settings or software on patient's computing device 142 that are not compatible with the requirements of the video call. A weak network connection to patient computing device 142 may also prevent the video call. Other factors may adversely affect the video call.

Authentication server 110 may authenticate healthcare provider 151, service provider 161, and/or patient 141. Messaging server 120 can send messages to computing devices such as patient computing devices 142. These messages may include links to video calls hosted by video server 130 or links to join video calls via audio conferencing only. In addition to hosting video calls, video server 130 can assess data connectivity to computing devices including any of the patient computing devices 142. More particularly, video server 130 can send test messages to patient computing devices 142, which are designed to gather information about software executing on the computing devices, user settings on the computing devices, processing bandwidth of the computing devices, data transmission bandwidth to the computing devices, etc. Video server 130 can evaluate the data connectivity between video server 130 and patient computing device 142 based on the information it gathers from responses to the test messages. Video server 130 can host a video call between patient 141, healthcare provider 151, and service provider 160 that involves an exchange of audio and video data with computing device 142 assuming sufficient data connectivity.

Figure 2:
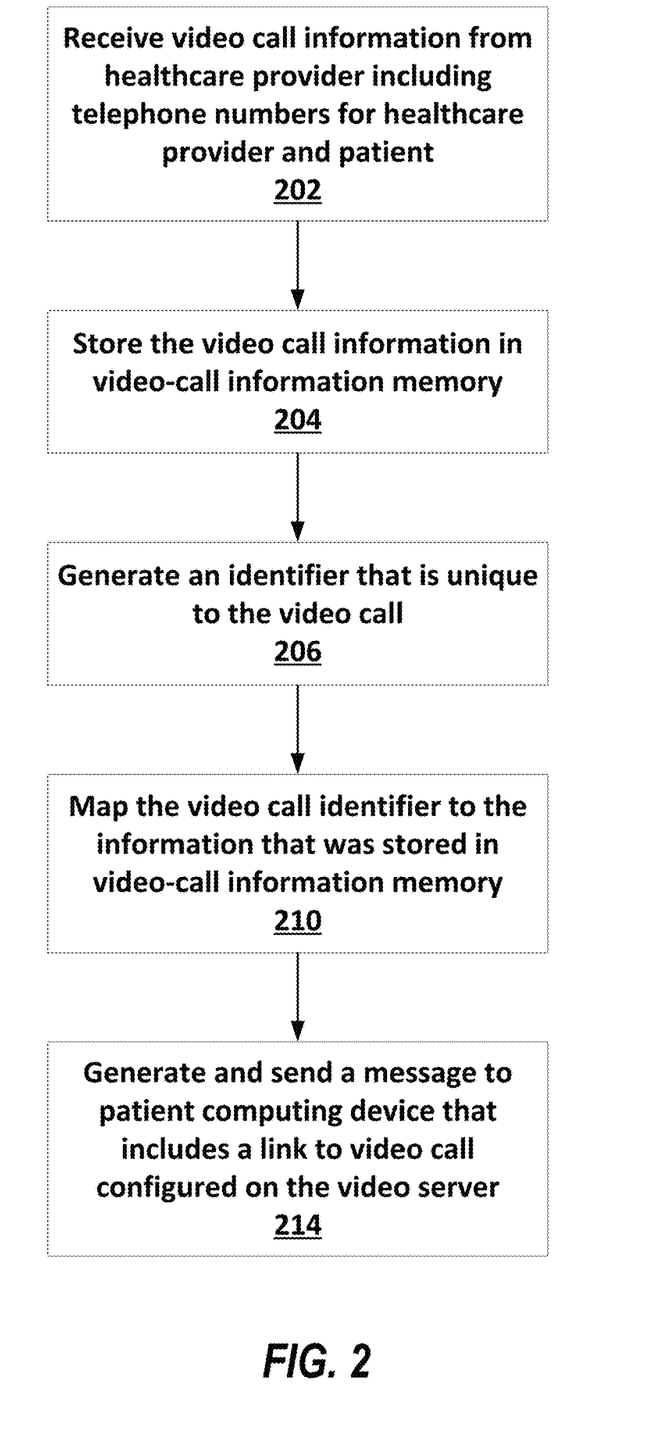
FIG. 2 is a flow diagram of an example process of setting up a video call in accordance with one or more embodiments of the disclosure.

System architecture 100 allows healthcare provider 151 to set up a video call, which involves sending patient computing device 142 a video call link that can be activated by patient 141. This link allows patient 141 to join a video call with healthcare provider 151, assuming sufficient data connectivity exits between video server 130 and the patient's computing device 142. FIG. 2 illustrates relevant aspects of a process for setting up a video call with patient 141. This process starts after healthcare provider 151 launches an app (e.g., an application, a program, etc.) on one of the healthcare provider's computing device 152. The app allows the healthcare provider 151 to set up a video call with patient 141. The app communicates with the video server 130, which in turn communicates with the messaging server 120. The app prompts the healthcare provider 151 for information related to the video call that may include: the health provider's name, the health provider's telephone number, the patient's name, the patient's telephone number for smart phone 142-1, the patient's email address for computer 142-2 or 142-3, etc. The video call information is received by video server 130 at step 202. At step 204 video server 130 stores the information in video-call information memory. Rather than using an app executing on healthcare provider's computing device 152, in an alternative embodiment, healthcare provider 151 can set up a video call with patient through a browser executing computing device 152.

The video server 130 configures the video call (also known as a virtual conference room) on video server 130. Configuration includes generating a unique identifier for the video call as shown in step 206. Video call server 130 also generates a link to the video call. The link may include access information for the video call, including the video call identifier generated in stop 206. In step 210 video server 130 maps the identifier generated in step 206 to the video call information that was stored in video-call information memory at step 204.

Video server 130 is in data communication with messaging server 120. Messaging server 120 receives video call configuration information from video server 130 including the link generated by video server 130 for the example video call, and other information related to the video call such as a telephone number for smart phone 142-1, email address for laptop computer 142-2, etc. The messaging server 120 sends a message to patient computing device 142 with the link generated by video server 130 in step 214. For example, the messaging server 120 may send a short message service (SMS) message with the link to patient smartphone 142-1, or messaging server 120 may send an email with the link to patient laptop computer 142-2, or both.

Figure 3:
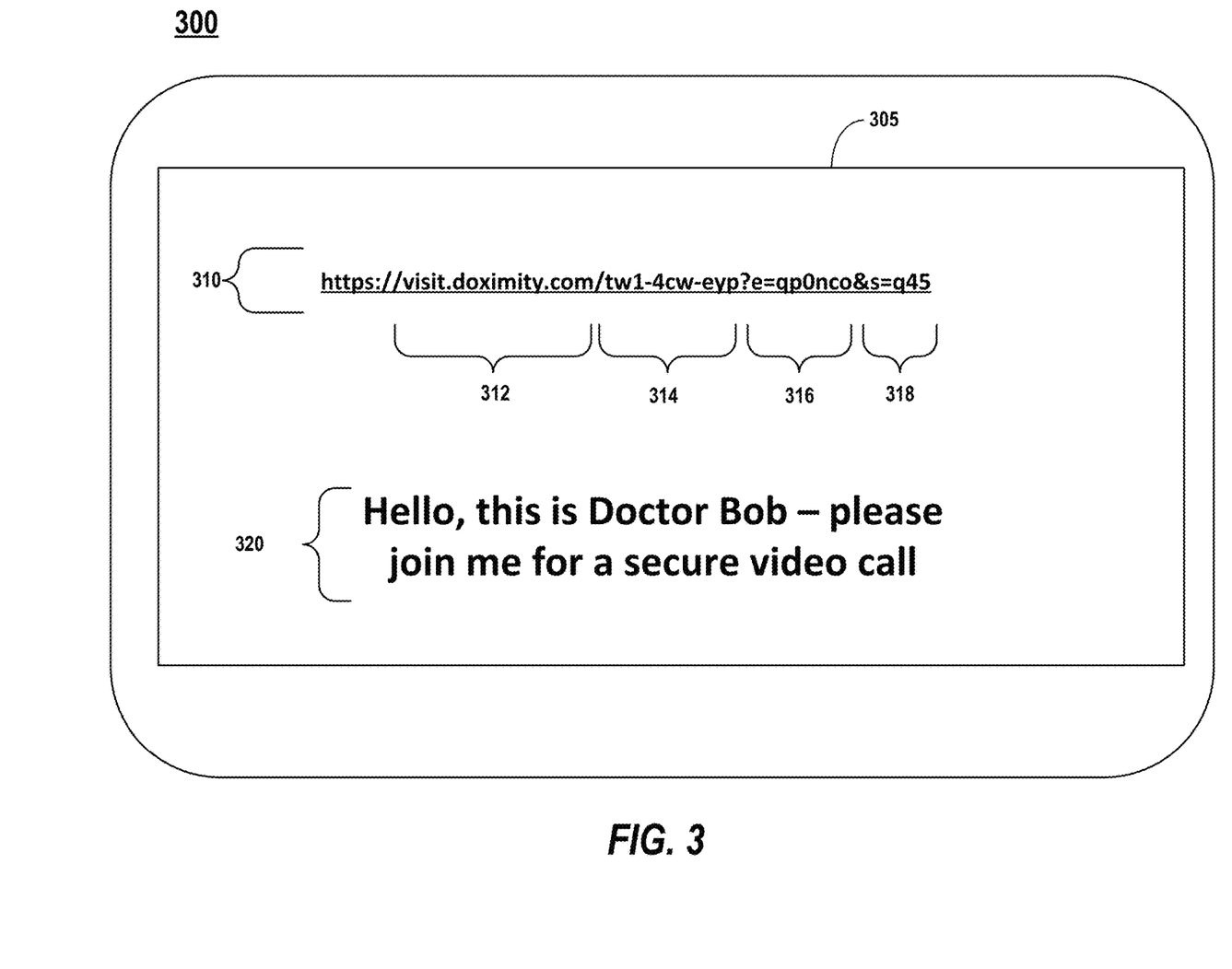
FIG. 3 is a diagram illustrating an example patient interface in accordance with one or more embodiments of the disclosure.

FIG. 3 is a diagram illustrating an example patient interface 300 displayed on patient device 142 when patient 141 opens the message sent by messaging server 120. Interface 300 displays example message 305 received from messaging server 120. The message 305 may indicate in text that healthcare provider 151 wants to initiate a video call with patient 141. The message 305 includes example link 310 and additional text 320. The additional text 320 may convey additional information related to the video call, such as the identity of the healthcare provider who is initiating the video call (e.g., a name of the healthcare provider 151), when the video call is scheduled to occur, the purpose of the video call (e.g., a checkup, a follow-up consultation, etc.). In one embodiment, the link 310 may be a uniform resources locator (URL). Although the present disclosure refers to a URL, other types of resource locators, identifiers, resource identifiers, etc., may be use in other embodiments.

The "https://" portion of the link 310 may indicate the communication protocol for the video call. For example, the "https://" portion indicates that a Hypertext Transfer Protocol (HTTP) communication channel along with transport layer security (TLS) is be used to join and support the video call over network 105.

The "visit.doximity.com" portion of the link 310 indicates a location 312 in the network for the video server 130 that hosts the video call. Different locations (e.g., different domain names) may be used to identify and locate different video servers. In some examples, the link may also include an indication of a path to route video data for the video call.

In one embodiment, the portion "tw1-4cw-eyp" of the link 310 may be the identifier 314 that is unique to the video call, which was generated in step 206 of FIG. 2. The identifier 214 should be unique within the domain name and/or video server 130. Identifier 314 should be linked to the video call information that is stored in video-call information memory, which can be accessible by servers 110, 120, 130, or 140. The format of the identifier 314 may vary in different embodiments. The "?" portion of the link 310 may be a separator between different portions of the link 210.

In one embodiment, the "e=qpOnco" portion of the of the link 310 may indicate or represent, a time or time period 316 for the video call. For example, the "e=qpOnco" portion may indicate a start time for the video call (e.g., a time when video call should start). In another example, the "e=qpOnco" portion may indicate a time frame in which the video call should occur (e.g., may indicate a start time and an end time for the video call). In a further example, the "e=qpOnco" portion may indicate an expiration time (e.g., a latest time) within which the patient is able to join or setup the video call.

The "e=qpOnco&s=q45" portion of the of the link 310 may be a signature 218 to help increase the security of the video call. The "e=qpOnco&s=q45" portion may prevent a malicious person from modifying the link 310. If the link 310 has been modified by the malicious user, the video server will reject the request to join or setup the video call if the signature does not match the signature obtained by the video server. The "e=qpOnco&s=q45" portion may also prevent unauthorized users from joining the video call. For example, the "e=qpOnco&s=q45" portion may be generated using various encryption and/or hashing algorithms. In one embodiment, the "e=qpOnco&s=q45" portion may be generated by hashing the previous portions of the link 310 using a hash-based message authentication code secure hash algorithm (HMAC-SHA). This may prevent a malicious person from guessing the signature in an attempt to join the video call.

Patient 141 can join the video call with healthcare provider 151 by activating link 310. Assuming sufficient data connectivity with patient's computing device 142, the video call may proceed with an exchange of data (e.g., video data, video frames, audio data, audio frames, etc.) between patient computing device 142 and healthcare provider computing device 152 via video server 120. Without sufficient data connectivity the video call might not proceed. When patient 141 activates link 310, a process can be implemented for evaluating data connectivity before starting the video call.

Figure 4:
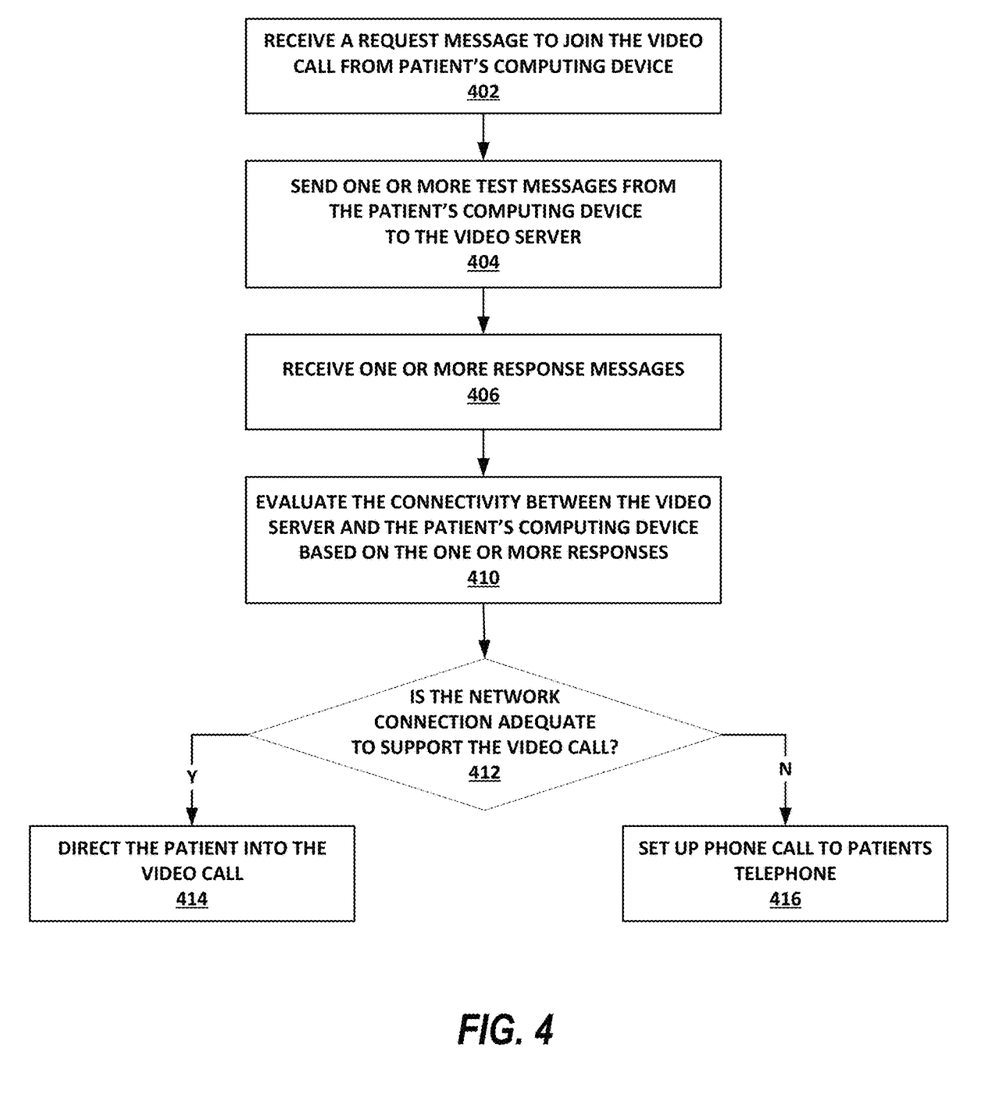
FIG. 4 is a flow diagram illustrating an example process for evaluating data connectivity between a patient computing device and a video call server in accordance with one or more embodiments of the disclosure.

FIG. 4 illustrates relevant aspects of an example process for assessing data connectivity in accordance with one aspect of the present disclosure. This process begins after patient 141 activates link 310, which prompts patient computing device 142 to send a request to video call server 130 to join the video call. In step 402 video server 130 receives the request from patient computing device 142 to join the video call.

A determination can be made as to whether the patient computing device 142 meets predetermined requirements to join the video call via videoconferencing. The determination can be made by the patient computing device 142, the video call server 130, by the patient computing device 142 acting in concert with the video call server 130, or by another device. For example, patient computing device 142 may send one or more messages for testing data connectivity to video server 130 as shown in step 404.

In an embodiment, patient computing device 142 may send a ping message that assesses the network path between video service 130 and computing device 142. Ping messages measure the round-trip time for messages sent from the source to a destination that are echoed back to the source. The round-trip time for the ping sent by computing device 142 can be used to assess the bandwidth of the network connection, and whether it can support the video call.

Patient computing device 142 may send a trace route message towards video call server 130. A traceroute can be used to track in real-time the pathway taken by a packet on network 105 from patient computing device 142 to video server 130, reporting the IP addresses of all the routers in between. Traceroute can also record the time taken for each hop the packet makes during its route to video call server 130.

Patient computing device 142 may send a message to test variations in data packet transmission delay to video call server 130, or the number of data packets that do not reach video call server 130 in a given time period.

In an embodiment, patient computing device 142 can send test messages to determine whether a firewall or virtual private network exists in the data communication path between video server 130 and patient computing device 142.

In step 406 patient computing device 142 can receive one or more responses from to the one or more test messages, respectively, that were sent in step 404. Patient computing device 142 can process data contained within the test messages and/or responses to determine whether the patient computing device 142 meets predetermined requirements to join the video call via videoconferencing. More particularly, the patient computing device 142 can determine whether the patient's computing device 142 can support a video call with video server 130 as shown in step 410. For example, the echo round-trip time to traverse network 105 from patient computing device 142 to video call server 130 and back, as identified in a ping message response, is compared to a predetermined threshold time value that is required to support a video call. Information received in other test message responses can also be processed to evaluate data connectivity between video call server 130 and patient computing device 142. In response to a determination that adequate connectivity exists the video call is started in step 414. In addition to the test messages, patient computing device 142 can determine if its browser and its version is compatible with video server 130. For example, the browser software available in patient computing device 142, is compared by patient computing device 142 to one or more browsers that are required by video server 130 to support a video call.

Figure 5:
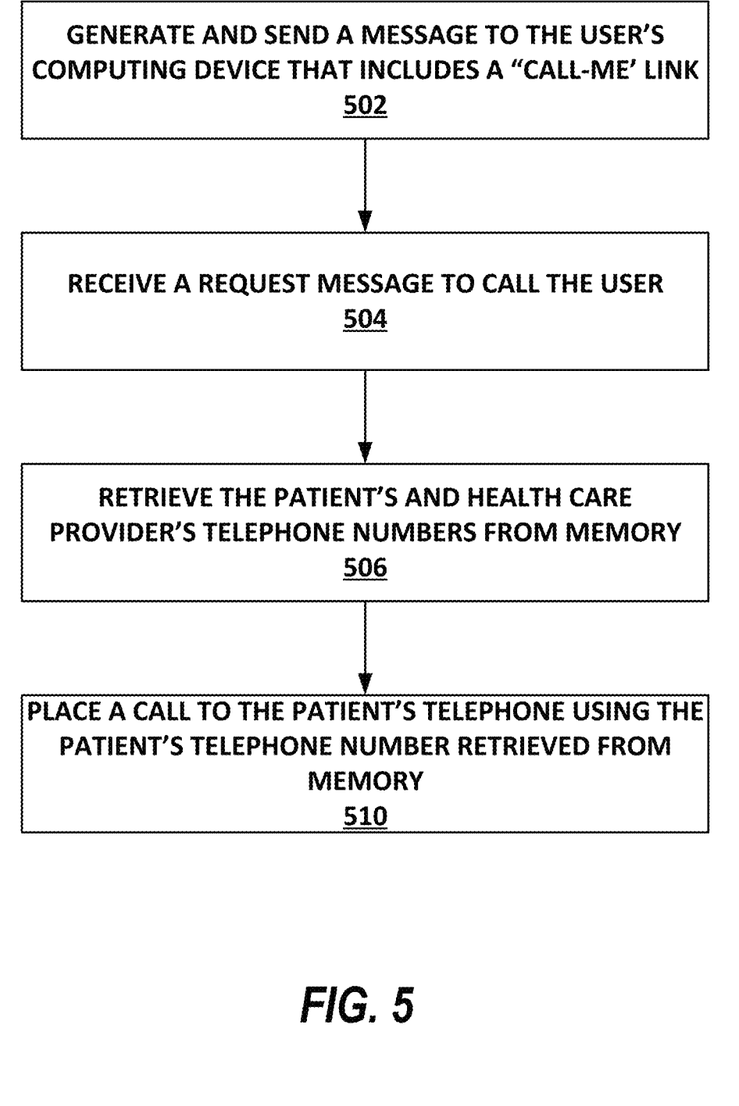
FIG. 5 is a flow diagram of an example process of setting up a telephone call in accordance with one or more embodiments of the disclosure.

In response to a determination that patient computing device 142 does not meet the predetermined requirements, and the video call to patient computing device 142 cannot be supported, patient computing device 142 can initiate a process to place a telephone from the video server to patient smart phone 142-1 as shown in step 416. FIG. 5 illustrates relevant aspects of a process for implementing step 416. At step 502, video call server 130 prompts messaging server 120 to generate and send a "call-me" message (e.g., an SMS message, a MMS message, a chat message, a text message, an email message, etc.) to patient's computing device 142. This message contains one or more links and text for display by patient computing device 142.

Figure 6:
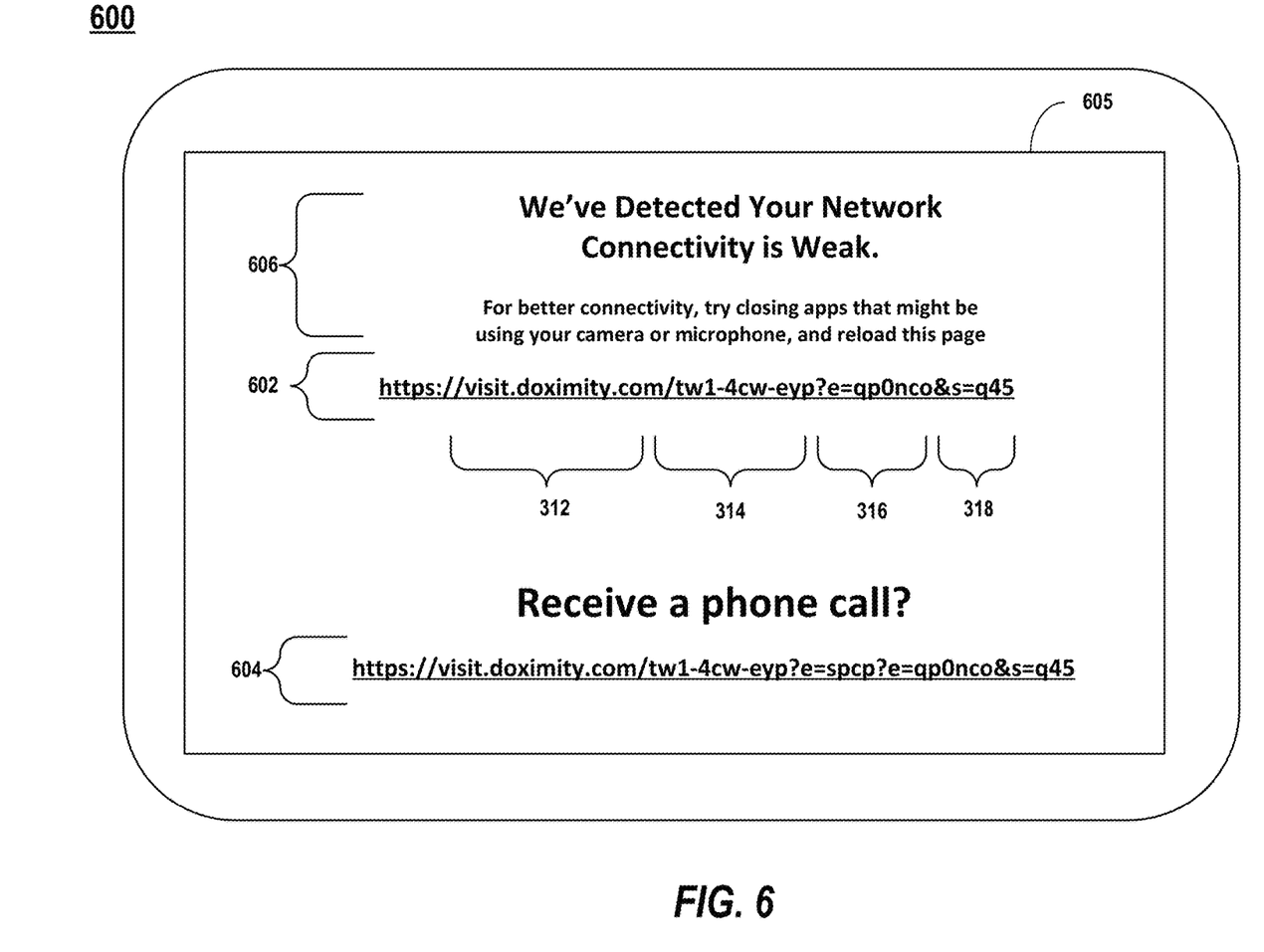
FIG. 6 is a diagram illustrating an example patient interface in accordance with one or more embodiments of the disclosure.

FIG. 6 illustrates an example patient interface 600 displayed on patient device 142 when patient 141 opens the message sent by messaging server 120 in step 502. Interface 600 displays an example call-me message 605 received from messaging server 120. The message 605 may include a text message 606 indicating weak data connectivity to patient computing device 142 has been detected. Another text message may indicate a firewall in the communication path between server 130 and computing device 142 may prevent the video call. Other text messages are contemplated.

Message 605 includes first and second links 602 and 604, respectively. First link 602 may be the same or similar link 310 that was provided in the message 305 of FIG. 3, which was previously displayed on patient's computing device 142. Text 606 can be positioned next to link 602, which indicates weak data connectivity and a suggestion (e.g., "try closing apps") for improving data connectivity. Link 602, when activated by patient 141, will reinitiate the process shown within FIG. 5. The second link 604 may be a URL, although other links are contemplated. Like link 305 shown in FIG. 3, the "visit.doximity.com" portion of the link 604 indicates the location for the video server 130. The portion "tw1-4cw-eyp" of the link 604 should be the same identifier shown in FIG. 3, which is unique to the video call and generated in step 206 of FIG. 2. The "e=spcp" portion of the of the link 604 may indicate or represent an instruction to initiate a phone call. The "e=qpOnco&s=q45" portion of the of the link 604 may be the same signature in link 305 shown in FIG. 3, which helps increase the security of the video call. This may prevent a malicious person from guessing the signature in an attempt to join the video call.

Patient 141 can optionally activate link 604, and in response patient computing device 142 sends a request message to video server 130. This message should include the video call identifier "tw1-4cw-eyp" and the portion "e=spcp" from link 604 that represents instruction to initiate a phone call. In step 504 video server receives the message generated and sent in step 502. In response, as shown in step 506, video server 130 access video-call information memory to read healthcare provider 151's phone number and patient 141's phone number for smart phone 142-1, which is mapped to video call identifier "tw1-4cw-eyp." Video call server 130 can then place a phone call to, for example, patient smartphone 142-1 in step 510. When patient 142 answers the phone call using smartphone 142-1, an audio-only communication channel (e.g., a cellular telephone channel) is established between smart phone 142-1 and the video call server 130. The established audio-only communication channel enables audio conferencing between patient 141 to visit with healthcare provider 151. Video server 130 can set up an alternative communication channel in step 510. For example, instead of placing a call to patient smartphone 141-2, video server 130 can place a VOIP call to a patient computing device 142-2 or 142-3 in step 510. Or video server 130 can set up text messaging with video server 130 in step 510.

Figure 7:
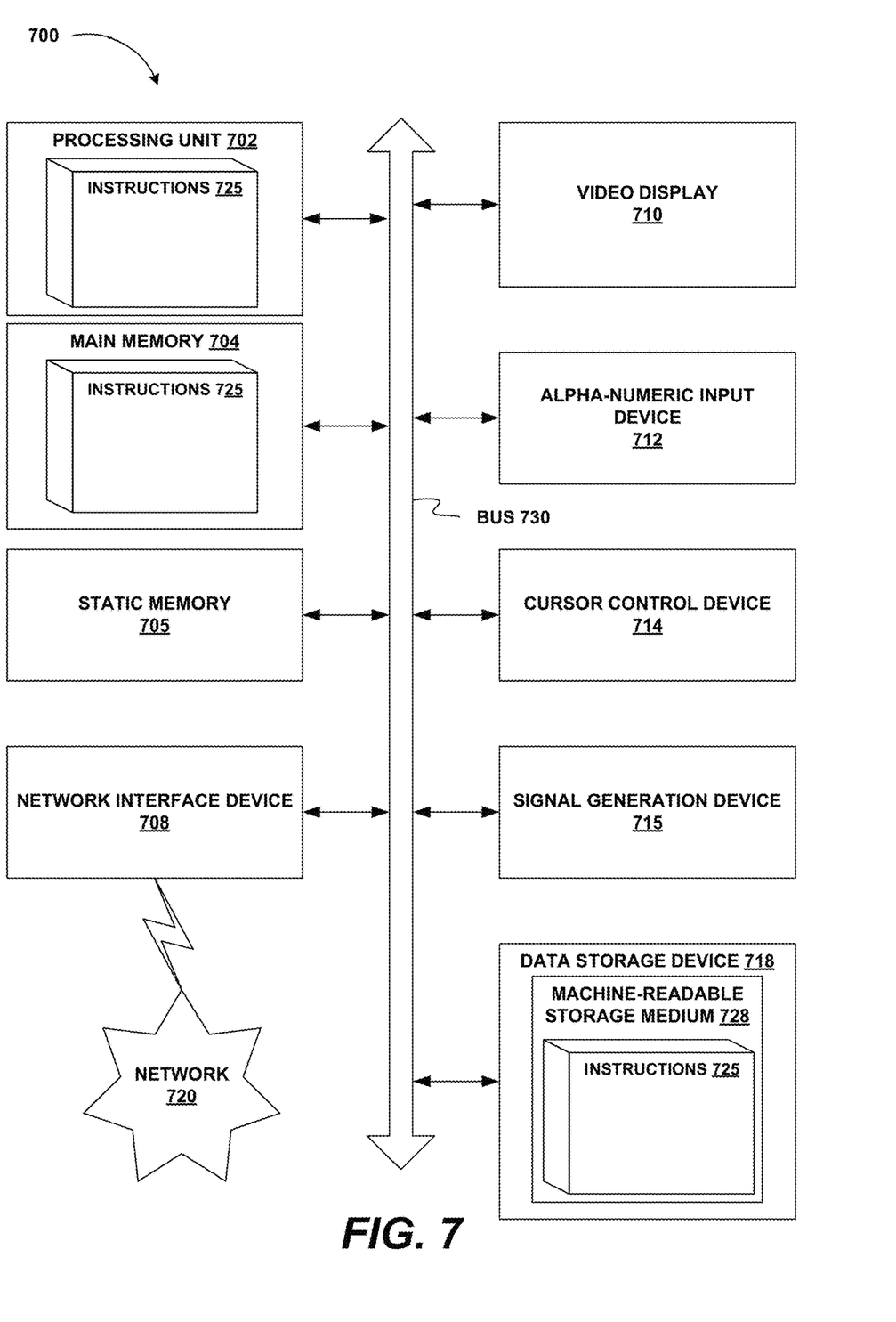
FIG. 7 is a block diagram of an example apparatus that may perform one or more of the operations described herein, in accordance with some embodiments of the present disclosure.

FIG. 7 is a block diagram of an example data processing device 700 that may perform one or more of the operations described herein, in accordance with some embodiments. Data processing device 700 may be connected to other data processing devices in a LAN, an intranet, an extranet, and/or the Internet. The data processing device may operate in the capacity of a server machine in the client-server network environment or in the capacity of a client in a peer-to-peer network environment. The data processing device may be provided by a personal computer (PC), a set-top box (STB), a server, a network router, switch or bridge, or any machine capable of executing a set of instructions (sequential or otherwise) that specify actions to be taken by that machine. Further, while only a single data processing device is illustrated, the term "data processing device" shall also be taken to include any collection of data processing devices that individually or jointly execute a set (or multiple sets) of instructions to perform the methods discussed herein.

The example data processing device 700 may include a processing unit (e.g., a general purpose processor, a PLD, etc.) 702, a main memory 704 (e.g., synchronous dynamic random access memory (DRAM), read-only memory (ROM)), a static memory 706 (e.g., flash memory and a data storage device 718), which may communicate with each other via a bus 730.

Processing unit 702 may be provided by one or more general-purpose processing devices such as a microprocessor, central processing unit, or the like. In an illustrative example, processing unit 702 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing unit 702 may also comprise one or more special-purpose processing devices such as an application specific integrated circuit (ASIC), a field programmable gate array (FPGA), a digital signal processor (DSP), network processor, or the like. The processing unit 702 may be configured to execute the operations described herein, in accordance with one or more aspects of the present disclosure, for performing the operations and steps discussed herein.

Data processing device 700 may further include a network interface device 708 which may communicate with a network 720. The data processing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse) and an acoustic signal generation device 716 (e.g., a speaker). In one embodiment, video display unit 710, alphanumeric input device 712, and cursor control device 714 may be combined into a single component or device (e.g., an LCD touch screen).

Data storage device 718 may include a computer-readable storage medium 728 on which may be stored one or more sets of instructions 725 that may include instructions for carrying out the operations described herein, in accordance with one or more aspects of the present disclosure. Instructions 725 may also reside, completely or at least partially, within main memory 704 and/or within processing unit 702 during execution thereof by data processing device 700, main memory 704 and processing unit 702 also constituting computer-readable media. The instructions 725 may further be transmitted or received over a network 720 via network interface device 708.

While computer-readable storage medium 728 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A method, comprising:
   sending a first message to a device, wherein the first message comprises a first link to join a video call, and wherein the first link includes a signature;
   receiving, from the device, a request to join the video call;
   determining, in response to receiving the request, whether the device meets predetermined requirements to join the video call via videoconferencing; and
   sending, in response to determining the device does not meet the predetermined requirements to join the video call via videoconferencing, a second message to the device, wherein the second message comprises text indicating that the device does not meet the predetermined requirements, the first link to join the video call, and a second link to join the video call via audio conferencing, and wherein the second link includes the signature.

2. The method of claim 1, wherein the second message includes a short message service (SMS) message comprising the second link to join the video call via audio conferencing.

3. The method of claim 1 further comprising:
receiving a request to join the video call via audio conferencing only in response to sending the second message to the device; and
initiating the telephone call in response to receiving the request to join the video call via audio conferencing.

4. The method of claim 3, wherein the telephone call is a voice over internet protocol (VOIP) telephone call.

5. The method of claim 1, wherein determining whether the device meets the predetermined requirements includes sending a network ping message, and receiving a network ping response message.

6. The method of claim 5:
wherein the network ping response message comprises an echo round-trip time;
wherein determining whether the device meets the predetermined requirements comprises comparing the echo round-trip time with a threshold value.

7. The method of claim 1, wherein determining whether the device meets the predetermined requirements includes identifying a browser executing on the device.

8. The method of claim 7, wherein determining whether the device meets the predetermined requirements comprises determining the browser executing on the device is incompatible with the video call via video conferencing.

9. The method of claim 1, wherein determining whether the device meets the predetermined requirements includes determining whether a network firewall exists in a communication path to the device.

10. The method of claim 3 further comprising:
storing a telephone number in memory before receiving, from the device, the request to join the video call;
in response to the receiving the request to join the video call via audio conferencing, accessing the memory to read the telephone number; and
wherein the telephone call is initiated using the telephone read from memory.

11. A non-transitory computer-readable medium storing instructions that, when executed by a processing device of a system, cause the system to:
send a first message to a device, wherein the first message comprises a first link to join a video call, and wherein the first link includes a signature;
receive, from the device, a request to join the video call;
determine, in response to receiving the request, whether the device meets predetermined requirements to join the video call via videoconferencing; and
send, in response to determining the device does not meet the predetermined requirements to join the video call via videoconferencing, a second message to the device, wherein the second message comprises text indicating that the device does not meet the predetermined requirements, the first link to join the video call, and a second link to join the video call via audio conferencing, and wherein the second link includes the signature.

12. The non-transitory computer-readable medium of claim 11, wherein the second message includes a short message service (SMS) message comprising the second link to join the video call via audio conferencing.

13. The non-transitory computer-readable medium of claim 12, wherein the stored instructions further cause the system to:
receive a request to join the video call via audio conferencing in response to sending the second message to the device; and
initiate the telephone call in response to receiving the request to join the video call via audio conferencing.

14. The non-transitory computer-readable medium of claim 11, wherein the computing device is the smartphone.

15. The non-transitory computer-readable medium of claim 12, wherein determining whether the device meets the predetermined requirements includes sending a network ping message, and receiving a network ping response message.

16. The non-transitory computer-readable medium of claim 13:
wherein the network ping response message comprises an echo round-trip time;
wherein determining whether the device meets the predetermined requirements comprises comparing the echo round-trip time with a threshold value.

17. The non-transitory computer-readable medium of claim 12, wherein determining whether the device meets the predetermined requirements includes identifying a browser executing on the device.

18. The non-transitory computer-readable medium of claim 15, wherein determining whether the device meets the predetermined requirements comprises determining the browser executing on the device is incompatible with the video call via video conferencing.

19. A system comprising:
a memory to store a telephone number; and
a processing device to:
send a first message to a device, wherein the first message comprises a first link to join a video call, and wherein the first link includes a signature;
receive, from the device, a request to join the video call;
determine, in response to receiving the request, whether the device meets predetermined requirements to join the video call via videoconferencing; and
send, in response to determining the device does not meet the predetermined requirements to join the video call via videoconferencing, a second message to the device, wherein the second message comprises text indicating that the device does not meet the predetermined requirements, the first link to join the video call, and a second link to join the video call via audio conferencing, and wherein the second link includes the signature.

20. The system of claim 19, wherein the processing device is further to:
receive a request to join the video call via audio conferencing in response to sending the second message to the device; and
initiate the telephone call in response to receiving the request to join the video call via audio conferencing.

* * * * *